United States Patent [19]
Yamada et al.

[11] Patent Number: 5,700,367
[45] Date of Patent: Dec. 23, 1997

[54] METHOD AND APPARATUS FOR CONTROLLING THE ENERGIZING OF A HEATER IN AN OXYGEN SENSOR

[75] Inventors: Tessho Yamada; Katsuhisa Yabuta; Takeshi Kawai; Hideki Toyoda, all of Aichi, Japan

[73] Assignee: NGK Spark Plug Co., Ltd., Nagoya, Japan

[21] Appl. No.: 636,401

[22] Filed: Apr. 23, 1996

[30] Foreign Application Priority Data

Apr. 28, 1995 [JP] Japan ................................. 7-105719

[51] Int. Cl.$^6$ ........................................ G01N 27/409
[52] U.S. Cl. ........................ 205/785; 204/408; 204/425; 204/426; 204/427; 205/784.5
[58] Field of Search ............................ 204/421–429; 205/784.5, 785, 783.5, 784

[56] References Cited

U.S. PATENT DOCUMENTS 4,359,030  11/1982  Sone et al. ............................ 204/425
4,694,809  9/1987  Nakano et al. ....................... 204/425

FOREIGN PATENT DOCUMENTS 0507115  10/1992  European Pat. Off. ..... G01N 27/419

OTHER PUBLICATIONS

Patent Abstracts Of Japan, vol. 9, No. 199 (P-380), Aug. 16, 1985, JP-A-60 063455 (Toyota Jidosha KK), Apr. 11, 1985, *abstract.
Patent Abstracts Of Japan, vol. 0, No. 00 JP-A-06 324017 (Matsushita Electric Ind Co), Nov. 25, 1994, *abstract.

*Primary Examiner*—T. Tung
*Attorney, Agent, or Firm*—Sughrue, Mion, Zinn, Macpeak & Seas, PLLC

[57] ABSTRACT

An oxygen sensor according to the present invention has battery element and a pump element in each of which porous electrodes are disposed on both faces of a solid electrolyte substrate. A minute current is supplied to the battery element after the start of energizing a heater and the activation of the sensor elements are judged on the basis of an interelectrode voltage generated at this energizing. A heater voltage is set to be 12V at the start of energizing. When the time period necessary for the interelectrode voltage to reach a predetermined voltage is short, the applied voltage is lowered to 11V. As a result, the time period necessary for judging the sensor elements to be activated can be made substantially constant irrespective of variations in sensor characteristics. After the activation judgment, the variation of the temperature of the sensor element is monitored on the basis of the interelectrode voltage. When the element temperature is varied, the heater voltage is raised or lowered so that the element temperature is stabilized.

13 Claims, 7 Drawing Sheets

METHOD AND APPARATUS FOR CONTROLLING THE ENERGIZING OF A HEATER IN AN OXYGEN SENSOR

BACKGROUND OF THE INVENTION

1. Field of the Invention

The present invention relates to a method and apparatus for controlling to energization of a heater for an oxygen sensor being provided with a sensor element in which porous electrodes are disposed on both ends of a solid electrolyte which is oxygen-ion-conductive, and the heater which activates the sensor element by heating.

2. Description of the Related Art

Conventionally, there has been an air-fuel ratio sensor for detecting the air-fuel ratio of an air-fuel mixture supplied to an internal combustion engine on the basis of the oxygen concentration of the exhaust gas of the engine. In this sensor, an oxygen sensor uses a sensor element in which porous electrodes are disposed on both faces of a plate-like solid electrolyte made of zirconia or the like.

An oxygen sensor of this type detects the oxygen concentration of the atmosphere based on the following phenomenon. When the partial pressure of oxygen in the atmosphere on one electrode side of the sensor element is different from that on the other electrode side, an electromotive force corresponding to the ratio of partial pressures of oxygen is generated across the electrodes and the sensor element functions as a so-called battery element. Alternatively, when a current is caused to flow through the sensor element by using the electrodes, oxygen is pumped from one electrode (negative electrode) into the other electrode (positive electrode) in accordance with the current and the sensor element functions as a so-called pump element. In either case, in order to detect the oxygen concentration by using such a sensor element, the temperature of the element has to be raised to a predetermined activation temperature of about 600° C. so that the sensor element is activated.

Conventionally, such an oxygen sensor is additionally provided with a heater for heating the sensor element. After energizing the heater is started to heat the sensor element, a minute current $i_{CP}$ (several mA) is supplied to the sensor element and a voltage appearing across the electrodes is detected as disclosed in, for example, Examined Japanese Patent Publication (Kokoku) No. HEI6-43986. When the detection voltage $V_S$ is lowered to a predetermined activation judging voltage $V_{SACT}$, or when a predetermined time period has elapsed after the detection voltage $V_S$ crosses a passing voltage $V_{SX}$ which is higher than the predetermined activation judging voltage $V_{SACT}$, it is judged that the sensor element is activated, and the operation of detecting the oxygen concentration is enabled.

Specifically, when the minute current $i_{CP}$ flows through the sensor element, if the electromotive force generated in accordance with the ratio of partial pressures of oxygen on the sides of both the electrodes is indicated by EMF, the interelectrode voltage $V_S$ is $V_S = i_{CP} \times Ri + EMF$. If the electromotive force EMF is previously known, it is possible to detect the internal resistance Ri which is lowered as the activation of the sensor element proceeds, on the basis of the interelectrode voltage $V_S$. Conventionally, therefore, the minute current $i_{CP}$ is caused to flow through the sensor element and the interelectrode voltage $V_S$ generated by the current is detected, thereby judging the activation of the sensor element, or in turn whether the air-fuel ratio of an internal combustion engine, etc. can be correctly detected by using the oxygen sensor or not.

When the sensor element is to be activated, conventionally, the energizing of the heater is not particularly controlled. A high voltage is merely applied to the heater in a range where a normal heating operation can be realized. Accordingly, even if a sensor element in which it is difficult to raise the temperature is used, the sensor element is activated within a desired time period. Consequently, a time period necessary for the sensor element to be activated after the start of energizing the heater to reach a state where the sensor can detect the oxygen concentration is largely varied in accordance with the characteristics of the heater and the sensor element which relate to the temperature rise.

In the case where a sensor element in which it is easy to raise the temperature (for example, a new sensor element) is used, particularly, the temperature of the sensor element is rapidly raised after the start of energizing the heater, whereby the time period necessary for activation is shortened and the temperature of the sensor element is excessively raised, the demand on the oxygen sensor is too high. Consequently, the matching between the oxygen sensor and an ECU for controlling the air-fuel ratio is lost, with the result that the air-fuel ratio control cannot be correctly performed.

SUMMARY OF THE INVENTION

It is an object of the invention to provide a method and apparatus for controlling the energizing of a heater for an oxygen sensor in which a time period necessary for a sensor element to be activated after the start of energizing can be made substantially constant irrespective of variations in characteristics of the heater and the sensor element, and the temperature of the sensor element can be prevented from being excessively raised.

A method of controlling the energizing of a heater for an oxygen sensor according to the present invention is used in the oxygen sensor which includes a first sensor element having a pair of porous electrodes disposed on both faces of a solid electrolyte being oxygen-ion-conductive, and a heater which is disposed in the vicinity of the sensor and which is energized to heat the first sensor element. In the method, the energizing of the heater to heat the first sensor element is started; a time period is measured from the start of the energizing until an interelectrode voltage generated between the pair of porous electrodes reaches an activation judging voltage; whether or not the first sensor element is activated based on the measured time period is judged; and an energizing condition hereafter of the heater is set based on the measured time period.

According to the invention, the starting characteristics of an oxygen sensor or the time period necessary for the sensor element to be energized after the start of heater energizing so as to be able to detect the oxygen concentration is not largely varied by variations in characteristics of the sensor element and the heater or can be stabilized at a substantially constant level.

PREFERRED EMBODIMENTS OF THE INVENTION

Hereinafter, an embodiment of the invention will be described with reference to the accompanying drawings.

Figure 1:
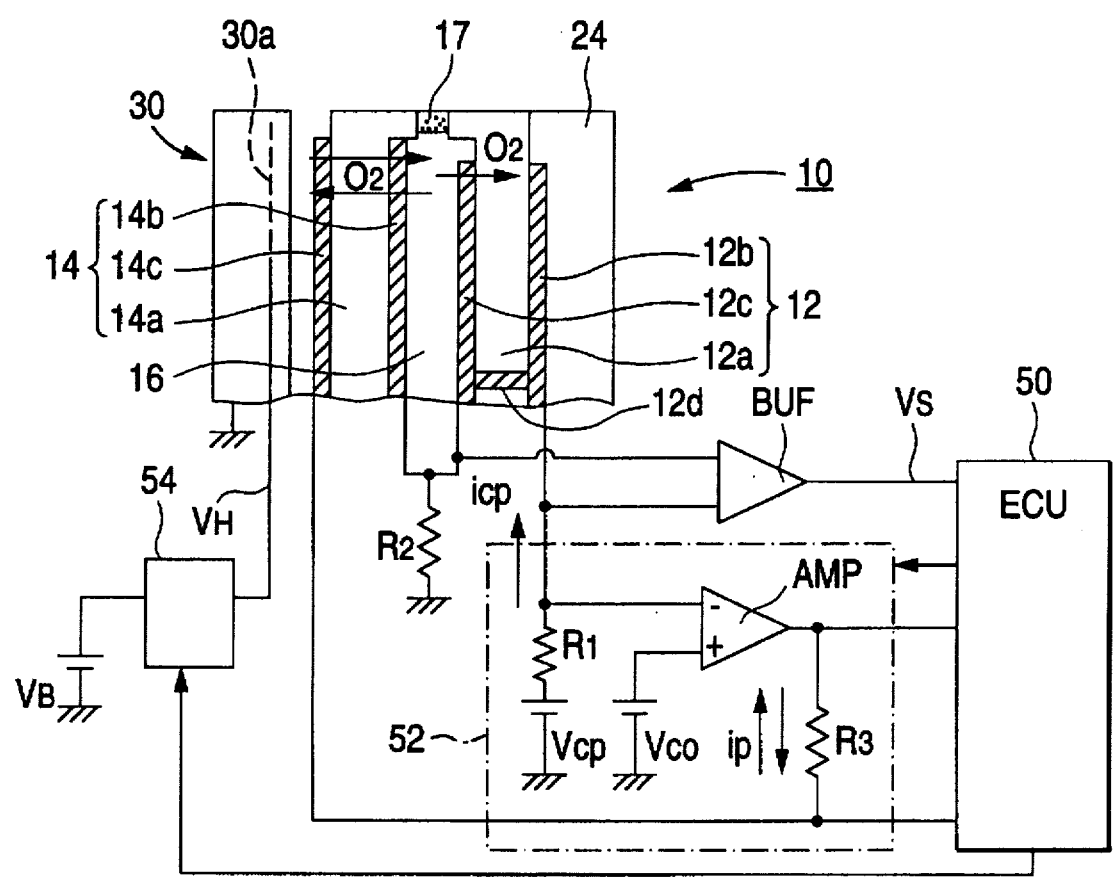
FIG. 1 is a schematic view showing an air-fuel ratio sensor of an embodiment and its peripheries.
Figure 2:
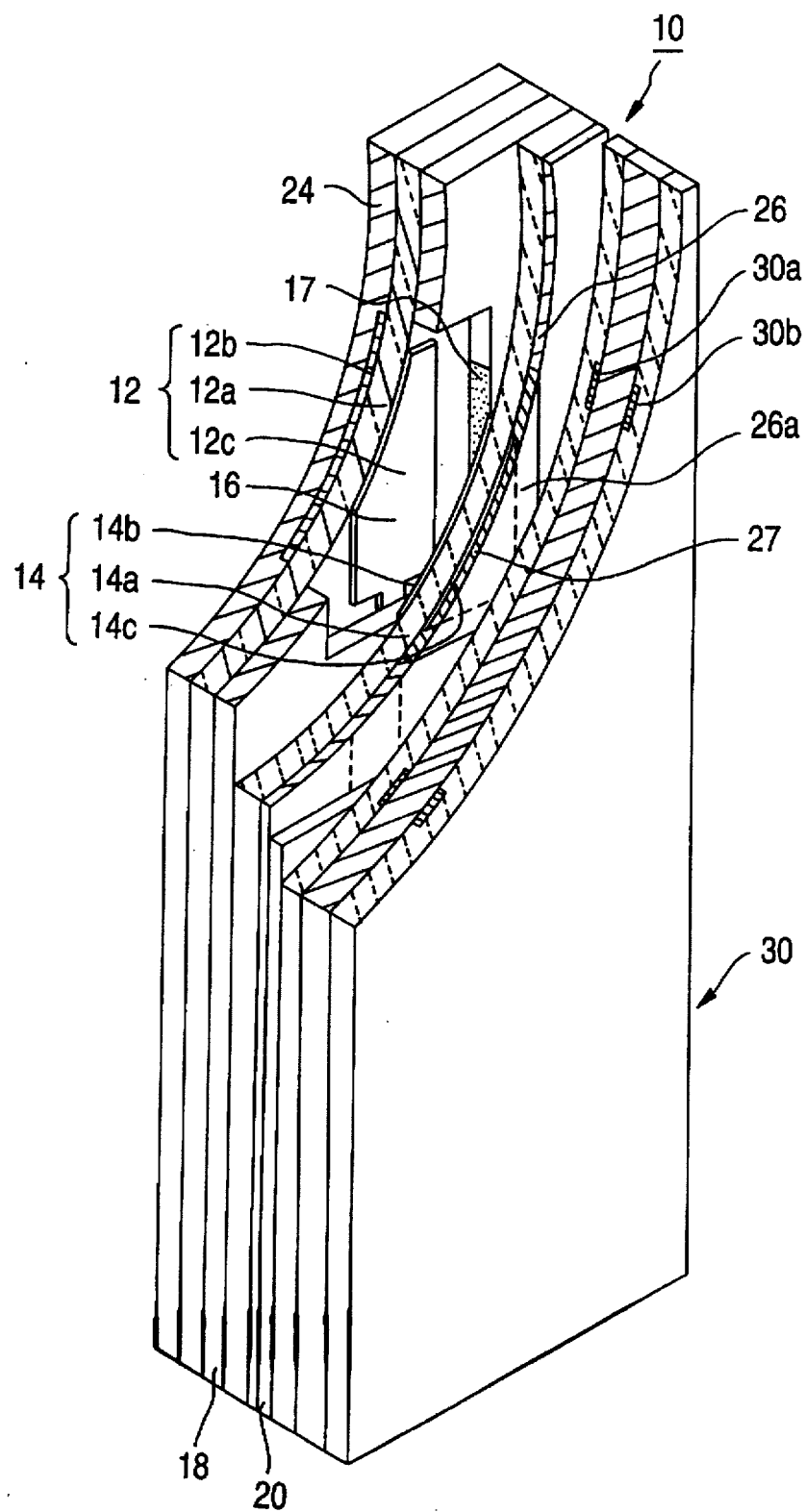
FIG. 2 is a partially cutaway perspective view of the air-fuel ratio sensor of the embodiment.

FIG. 1 is a schematic view showing an air-fuel ratio sensor to which an embodiment of the invention is applied and its peripheries, and FIG. 2 is a partially cutaway perspective view of the air-fuel ratio sensor.

An air-fuel ratio sensor 10 of the embodiment is attached to an exhaust pipe of an internal combustion engine, and detects the air-fuel ratio of an air-fuel mixture supplied to the internal combustion engine on the basis of the oxygen concentration of the exhaust gas. As shown in FIG. 2, the sensor 10 includes a battery element (first sensor element) 12, a pump element (second sensor element) 14 and a spacer 20. In the battery sensor element 12, porous electrodes 12b and 12c are disposed on both sides of a solid electrolyte substrate 12a. In the pump element 14, porous electrodes 14b and 14c are similarly disposed on both sides of a solid electrolyte substrate 14a. The spacer 18 is disposed between the elements 12 and 14 so as to form a measurement gas chamber 16. A heater 30 for heating the elements 12 and 14 is attached to the outer side of the pump element 14 with being separated therefrom by a spacer 20 so as to form a predetermined gap.

In each of the battery element 12 and the pump element 14, rectangular porous electrodes 12b and 12c or 14b and 14c are formed on both faces of the solid electrolyte substrate 12a or 14a made of an yttria-zirconia solid solution, respectively. Each of the porous electrodes 12b, 12c, 14b, and 14c is configured so that the common base is made of an yttria-zirconia solid solution and the remaining portion is made of platinum. As the material of the solid electrolyte substrates 12a and 14a, known is a calcia-zirconia solid solution in addition to an yttria-zirconia solid solution. Alternatively, a solid solution of cerium dioxide, thorium dioxide, or hafnium dioxide, a perovskite solid solution, a solid solution of a trivalent-metal oxide, or the like may be used.

The outer side of the pump element 14 is covered with an insulating layer 26 which is made of alumina having a hollow portion 26a corresponding to the porous electrode 14c. In the hollow portion 26a, a porous electrode protective layer 27 which is mainly made of alumina is formed to cover the porous electrode 14c so as to externally protect it.

The measurement gas chamber 16 is formed by bonding the battery element 12 with the pump element 14 while disposing the spacer 18 having a hollow portion corresponding to the porous electrodes 12c and 14b therebetween. The porous electrodes 12c and 14b are exposed to the inside of the measurement gas chamber 16 configured by the hollow portion. As the material of the spacer 18, alumina, spinel, forsterite, steatite, zirconia, etc. may be used.

In the spacer 18, a plurality of communicating holes through which the measurement gas chamber 16 communicates with the exterior are provided. Each of the communicating holes is filled with a porous filling material made of alumina so as to form a gas diffusion restriction layer 17, thereby controlling the flow of the measured gas into the measurement gas chamber 16 and the like.

A shield 24 made of a solid electrolyte is pasted on the outer side of the battery element 12 to cover the porous electrode 12b. Consequently, when a minute current $i_{CP}$ is caused by a detection circuit 52 which will be described later to flow from the porous electrode 12b t6 the porous electrode 12c, oxygen pumped into the porous electrode 12b is prevented from being discharged as it is. In the battery element 12, a leak resistance portion 12d is formed so as to allow a part of oxygen pumped into the porous electrode 12b to leak toward the measurement gas chamber 16 (see FIG. 1). As a result of the supply of the minute current $i_{CP}$ conducted by the detection circuit 52, the porous electrode 12b has a constant oxygen concentration. Therefore, an electromotive force EMF corresponding to the oxygen concentration in the measurement gas chamber 16 with respect to that in the porous electrode 12b is generated in the battery element 12.

A heating pattern 30a is formed on one side of the heater 30, i.e., the side opposing the pump element 14. A well-known migration preventing pattern 30b is formed on the other side.

Referring to FIG. 1, the control system which controls the air-fuel ratio sensor 10 and judges the activation of the sensor elements 12 and 14 will be described.

As shown in FIG. 1, the porous electrodes 12c and 14b of the battery element 12 and the pump element 14 which contact with the measurement gas chamber 16 are grounded through a resistor $R_2$. The other porous electrodes 12b and 14c are connected to the detection circuit 52. In the detection circuit 52, the porous electrode 12b on the side of the shield 24 is connected to one end of a resistor $R_1$. A constant voltage Vcp is applied to the other end of the resistor R1. The resistor R1 is used for supplying the minute current $i_{CP}$ which is substantially constant to the battery element 12, and has a value which is sufficiently greater than that of the resistor R2 and the internal resistance of the battery element 12.

The end of the resistor R1 in the side of the porous electrode 12b is connected also to the inverting input terminal of a differential amplifier AMP. A reference voltage $V_{CO}$ is applied to the non-inverting input terminal of the differential amplifier AMP. Consequently, the differential amplifier AMP outputs a voltage which corresponds to the difference between the reference voltage $V_{CO}$ and the voltage of the porous electrode 12b of the battery element 12. The output of the differential amplifier AMP is connected through a resistor R3 to the porous electrode 14c of the pump element 14 which is on the side of the heater 30. As a result, a pump current $i_P$ bidirectionally flows through the pump element 14 in accordance with the output of the differential amplifier AMP.

In other words, the detection circuit 52 causes the minute current $i_{CP}$ to flow through the battery element 12 so that oxygen is pumped into the porous electrode 12b. As a result, the porous electrode 12b functions as an internal oxygen reference source so that a voltage corresponding to the oxygen concentration in the measurement gas chamber 16 is generated across the battery element 12. Furthermore, the differential amplifier AMP supplies the pump current $i_P$ to the pump element 14 so that the voltage (more correctly, including the voltage across the resistor R2) is equal to the reference voltage $V_{CO}$, thereby controlling the oxygen concentration in the measurement gas chamber 16 so as to be kept constant.

The pump current $i_p$ generated as a result of this control corresponds to the oxygen concentration of the surrounding measured gas atmosphere. Therefore, the pump current $i_p$ is converted into a voltage signal by the resistor R3. The voltage signal is supplied as a detection signal indicating the oxygen concentration of the exhaust gas and in turn the air-fuel ratio, to an electronic control unit (hereinafter, referred as "ECU") 50 which controls the internal combustion engine and is composed of a microcomputer, etc.

While the internal combustion engine is started to operate, the detection circuit 52 is powered on so that the minute current $i_{CP}$ is started to supply to the battery element 12. The operation of the differential amplifier AMP which controls the pump current $i_P$ is enabled and disabled by the ECU 50. The operation is disabled until the ECU 50 judges that the air-fuel ratio sensor 10 is activated. The detection circuit which controls the pump current $i_P$ as described above and detects the oxygen concentration (the air-fuel ratio) is well known. Therefore, the detailed description of the circuit is omitted.

A heater voltage $V_H$ is applied through a voltage switchover circuit 54 to the heating pattern 30a of the heater 30. The voltage switchover circuit 54 receives a battery voltage $V_B$ and supplies a power to the heater 30. As the heater voltage $V_H$ to be applied to the heater 30, the voltage switchover circuit 54 can selectively output either of 12V which is directly obtained from the battery voltage $V_B$, and 11V and 10V which are obtained by lowering the battery voltage $V_H$. In accordance with a voltage switchover instruction issued by the ECU 50, one of the voltages (12V, 11V, and 10V) is applied as the heater voltage $V_H$ to the heating pattern 30a.

A buffer circuit BUF through which the voltage (the interelectrode voltage) across the porous electrodes 12b and 12c is supplied to the ECU 50 is connected to the battery element 12. The buffer circuit BUF and the resistor R1 constitute the voltage detecting unit in the present invention.

While the internal combustion engine is started to operate, the ECU controls the voltage switchover circuit 54 so as to apply the heater voltage $V_H$ to the heating pattern 30a of the heater 30, thereby heating the battery element 12 and the pump element 14. The ECU 50 judges whether or not the sensor elements 12 and 14 are activated by the heating based on the interelectrode voltage $V_S$ of the battery element 12 which is supplied from the buffer circuit BUF. After the activation judgment, the ECU 50 starts to detect the air-fuel ratio by using the air-fuel ratio sensor 10, and to control the air-fuel ratio of the internal combustion engine based on the detection result.

Next, among various control processes executed by the ECU 50, principal processes relating to the present invention, i.e., the heater control for activating the sensor elements, and the stabilization control for stabilizing the temperatures of the sensor elements after activation will be described with reference to flowcharts shown in FIGS. 3 and 4.

Figure 3:
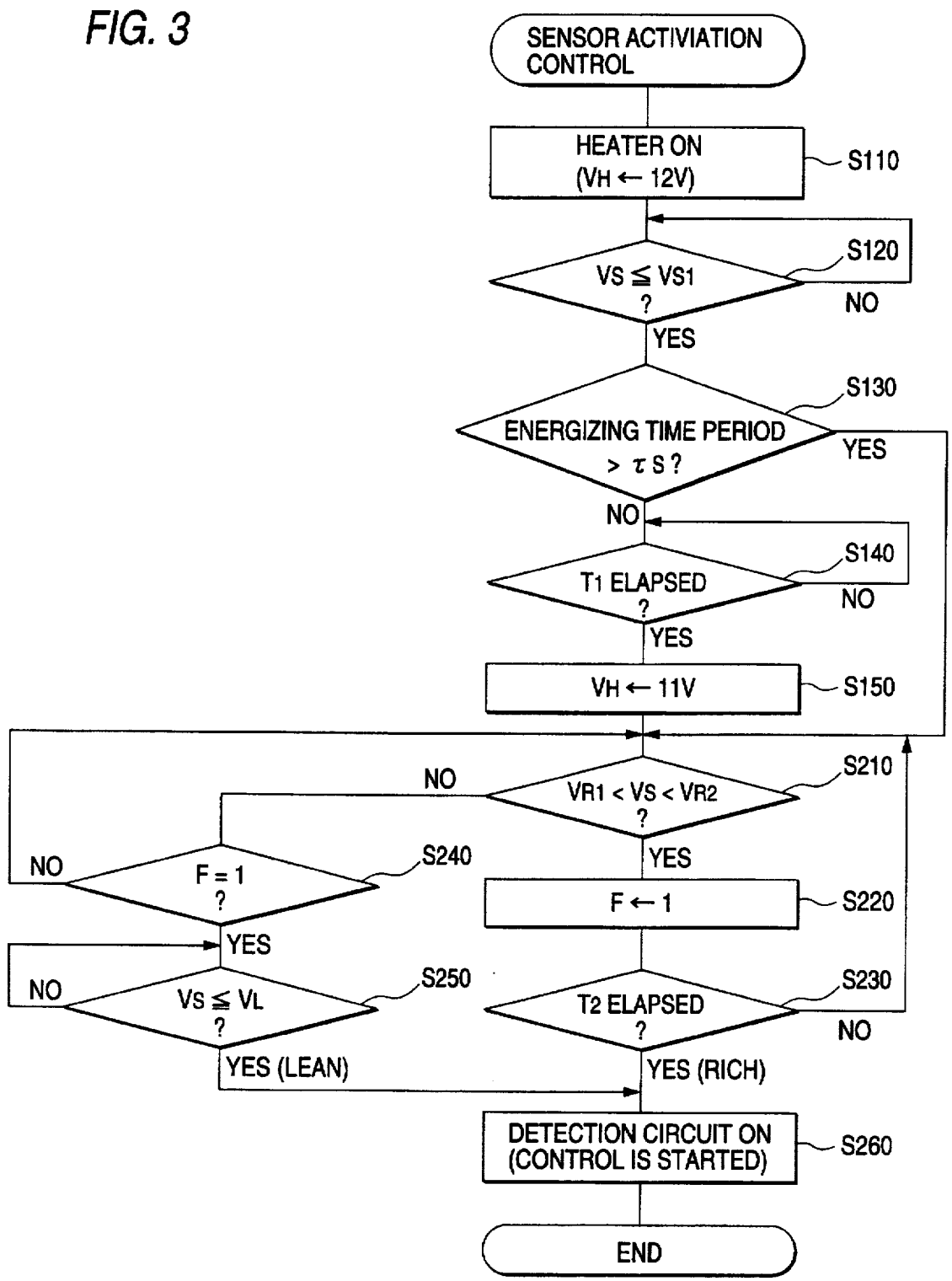
FIG. 3 is a flowchart showing a sensor activation control process which is executed by an ECU in the embodiment.

FIG. 3 shows the sensor activation control which is started at the same time when the internal combustion engine is started to operate and then executed until the sensor elements 12 and 14 are judged to be activated. As shown in FIG. 3, when the internal combustion engine is started to operate, the voltage switchover circuit 54 outputs the heater voltage $V_H$ in S110 (where "S" means a step) which is 12V so that energizing of the heater 30 is started (turned on). At the same time, operation of an integrated timer begins so as to measure the time period of energizing the heater.

In next S120, it is judged whether or not the interelectrode voltage $V_S$ supplied from the buffer circuit BUF is lowered, as a result of the temperature rise of the battery element 12 caused by the energizing, to a level which is not higher than a predetermined voltage $V_{S1}$ (for example, 1.3V). The operation waits until the interelectrode voltage $V_S$ is lowered to the predetermined voltage $V_{S1}$ or less.

When interelectrode voltage $V_S$ is lowered to the predetermined voltage $V_{S1}$ or less, the operation proceeds to S130. The heater energizing time period is read out by the integrated timer which is started at the start of the heater energizing so as to judge as to whether or not the read out time period is longer than a preset judgment time period $\tau S$.

If it is judged in S130 that the heater energizing time period is longer than the judgment time period $\tau S$, the operation jumps to S210 so that the heater voltage $V_H$ is maintained to 12V. If it is judged that the heater energizing time period is not longer than the judgment time period $\tau S$, the operation waits in S140 until a predetermined heating time period T1 is elapsed, and then the heater voltage $V_H$ is in S150 switched to 11V. Thereafter, the operation proceeds to S210.

In S210, it is judged whether or not the interelectrode voltage $V_S$ of the battery element 12 is lowered as a result of the reduction of the internal resistance due to the heating to be in a voltage range ($V_{R1} < V_S < V_{R2}$) from a voltage $V_{R1}$ (for example, 0.6V) which is a preset activation judging voltage in a rich air-fuel ratio region to another voltage $V_{R2}$ (for example, 0.9V). If the interelectrode voltage $V_S$ is within this voltage range, a flag F indicating that the interelectrode voltage $V_S$ enters the voltage range is set in S220. In next S230, it is judged whether or not the time period while the interelectrode voltage $V_S$ is in the voltage range reaches a preset rich judgment time period T2.

If it is judged in S230 that the time period while the interelectrode voltage $V_S$ is in the voltage range ($V_{R1} < V_S < V_{R2}$) reaches the rich judgment time period T2, the sensor elements 12 and 14 are judged to be activated in the exhaust gas in the rich air-fuel ratio region in which little oxygen exists, and the operation proceeds to S260. In contrast, if it is judged in S230 that the time period fails to reach the rich judgment time period T2, the operation returns to S210.

If it is judged in S210 that the interelectrode voltage $V_S$ is not in the voltage range ($V_{R1} < V_S < V_{R2}$), the operation proceeds to S240 where it is judged whether the flag F is set or not. The flag F indicates whether the interelectrode voltage $V_S$ once entered the voltage range. If the flag F is reset and the interelectrode voltage $V_S$ is not yet lowered to the voltage range after the heating of the sensor elements 12 and 14, the operation returns to S210.

If it is judged in S240 that the flag F is set, i.e., after the start of energizing the heater 30, the interelectrode voltage $V_S$ once entered the voltage range and is further lowered, the operation proceeds to S250. It is then judged whether or not the interelectrode voltage $V_S$ is lowered to a level which is not higher than a preset activation judging voltage $V_L$ (for example, 0.2V) in a lean air-fuel ratio region. The operation waits until the interelectrode voltage $V_S$ is lowered to the activation judging voltage $V_L$ or less. When the interelectrode voltage $V_S$ is lowered to the activation judging voltage $V_L$ or less, the sensor elements 12 and 14 are judged to be activated in the exhaust gas in the lean air-fuel ratio region in which oxygen exists abundantly, and the operation proceeds to S260.

Finally, in S260, the differential amplifier AMP of the detection circuit 52 is turned on so that the detection circuit 52 starts the operation of detecting the air-fuel ratio.

Figure 4:
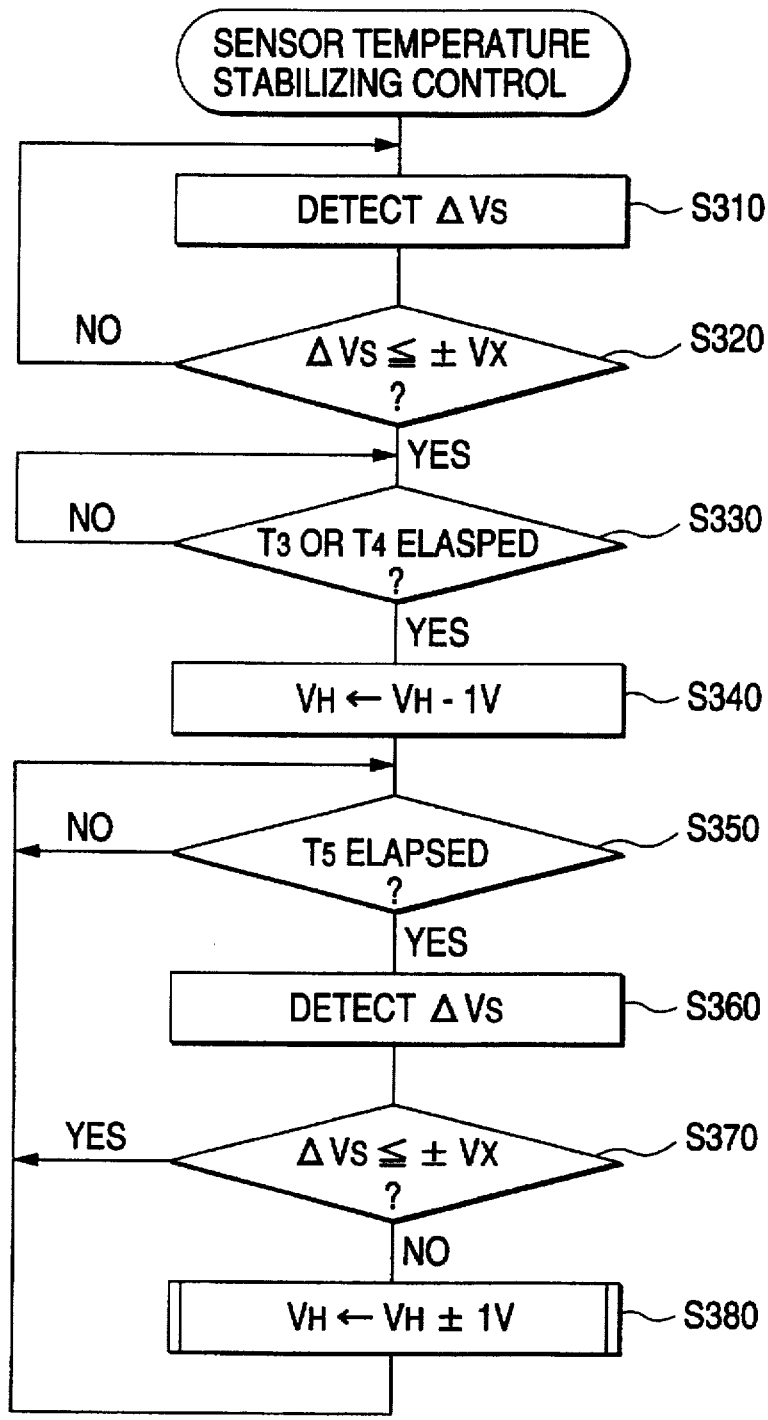
FIG. 4 is a flowchart showing a sensor temperature stabilizing control process in the embodiment.

FIG. 4 shows a sensor temperature stabilizing control process which is repeatedly executed by the ECU 50 together with the various control processes for controlling the air-fuel control, during a period continuing from when the sensor elements 12 and 14 are judged to be activated in the sensor activation control process and the detection circuit 52 starts the detection of the air-fuel ratio and until when the operation of the internal combustion engine is stopped.

As shown in FIG. 4, when the process is started, an error $\Delta V_S$ of the interelectrode voltage $V_S$ of the battery element 12 from the target voltage is detected in S310. Namely, the detection circuit 52 controls the pump current $i_P$ flowing through the pump element 14 so that the interelectrode voltage $V_S$ is equal to the predetermined target voltage (for example, 0.45V). The control error of this control is detected from the deviation $\Delta V_S$ of the interelectrode voltage $V_S$ from the target voltage.

In next S320, it is judged whether or not the detected error $\Delta V_S$ is within a preset allowable range $\pm V_X$ (for example, ±0.1V). If the error $\Delta V_S$ is within the allowable range $\pm VX$, it is judged that the pump current $i_P$ is properly controlled by the operation of the detection circuit 52, and the operation proceeds to S330. If the error $\Delta A_S$ is not within the allowable range $\pm V_X$, it is judged that the detection circuit 52 fails to properly control the pump current $i_P$, and the operation returns to S310. Then the operation waits until the pump current $i_P$ is properly controlled, while repeatedly executing S310 and S320. In other words, in the processes of S310 and S320, the operation waits until the time period when the control is stabilized or the response time period is elapsed, after the start of the control of the pump current $i_P$.

In S330, when the heater voltage $V_H$ which is currently applied to the heater 30 is 12V, a time period T3 is measured, and, when the heater voltage $V_H$ is 11V, a time period T4 (T4>T3) is measured, so that the operation waits until the predetermined time period T3 or T4 is elapsed. When the predetermined time period T3 or T4 is elapsed, the heater voltage $V_H$ is changed in S340 to be 11V or 10V which is lower than the current voltage by 1V. In next S350, it is judged whether a predetermined time period T5 (T5>T4 and T3) is further elapsed or not, so that the operation waits for the temperatures of the sensor elements 12 and 14 to have a value corresponding to the changed heater voltage $V_H$. In next S360, the control error $\Delta V_S$ of the interelectrode voltage $V_S$ is detected in the same manner as S310 described above.

In next S370, it is judged whether the detected error $\Delta V_S$ is within the allowable range $\pm V_X$ or not. If the error $\Delta V_S$ is within the allowable range $\pm V_X$, it is judged that the sensor elements 12 and 14 are controlled by the currently set heater voltage $V_H$ to be within the temperature range in which the air-fuel ratio can be properly detected, and the operation returns to S350. If the error $\Delta V_S$ exceeds the allowable range $\pm V_X$, it is judged that the sensor elements 12 and 14 are not controlled by the currently set heater voltage $V_H$ to be within the temperature range in which the air-fuel ratio can be properly detected, and the operation proceeds to S380.

In S380, when the heater voltage $V_H$ is 11V or 12V which is lower by 1V than the initial voltage set in the activation judgment, the heater voltage $V_H$ is raised by 1V so as to be returned to the initial voltage 12V or 11V. When the heater voltage $V_H$ is 12V or 11V which is the initial voltage set in the activation judgment, the heater voltage $V_H$ is lowered by 1V and the sensor temperature stabilizing control is started. Thereafter, the heater voltage $V_H$ is returned to 11V or 12V which has been initially set in S340. As a result of the above-described sequence, the heater voltage $V_H$ is raised or lowered by 1V, and the operation returns to S350.

As described above, in the embodiment, the heater voltage $V_H$ is controlled in the following manner. In the sensor temperature stabilizing control process, the heater 30 is energized at the heater voltage $V_H$=12V while the internal combustion engine is started to operate so as to start the heating of the sensor elements 12 and 14. Thereafter, the heater energizing time period continuing until the interelectrode voltage $V_S$ of the battery element 12 reaches the predetermined voltage $V_{S1}$ as the temperatures of the sensor elements 12 and 14 are raised (that is, the internal resistances are lowered) is measured. When the measured heater energizing time period is longer than the judgment time period τS, the heater voltage $V_H$ is kept to be as it is or 12V. When the time period is not longer than the judgment time period τS, the heater voltage $V_H$ is lowered to 11V.

Figure 5:
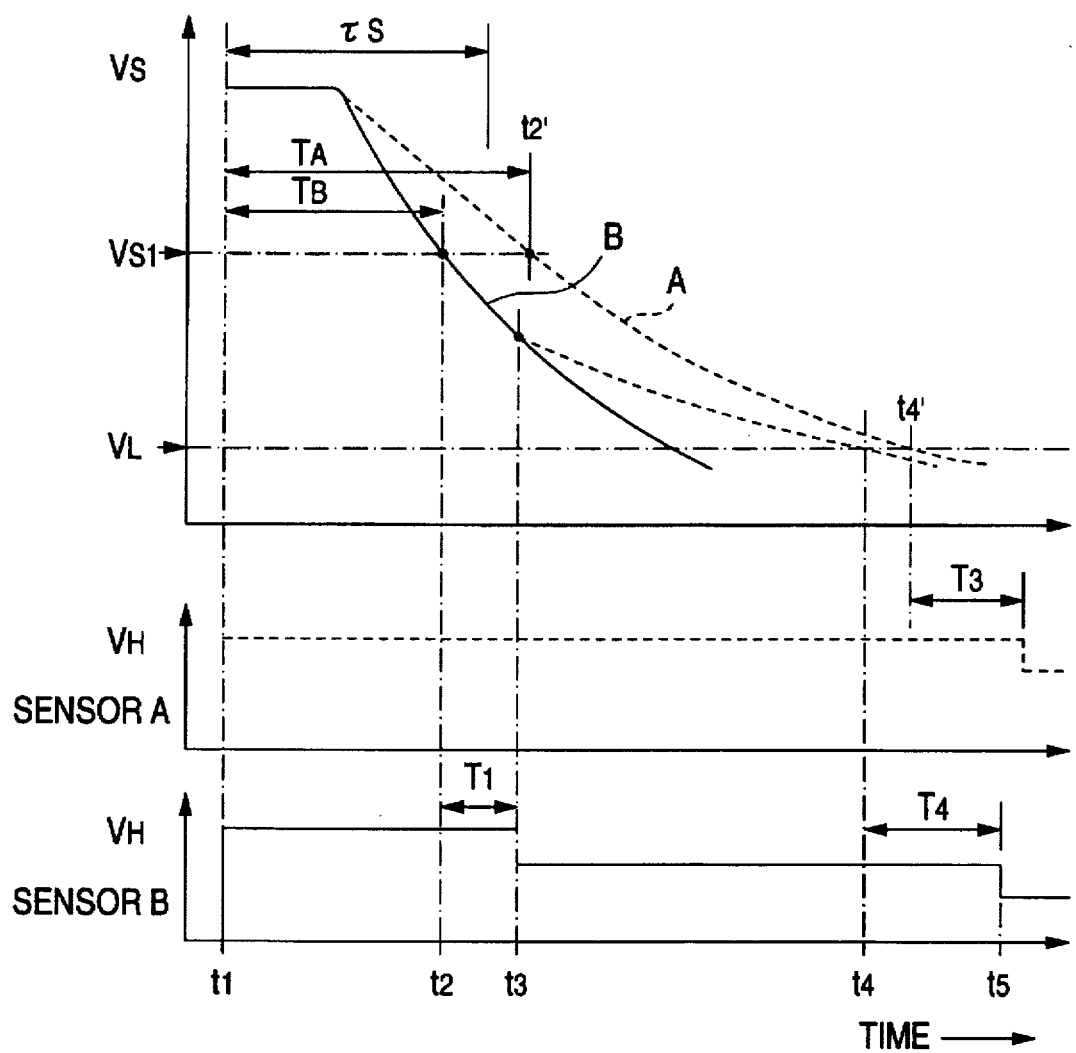
FIG. 5 is a time chart illustrating the variation of the interelectrode voltage of a battery element in the sensor of the embodiment and a control operation for the sensor.

As a result, as shown in FIG. 5, in an air-fuel ratio sensor A in which the heater energizing time period continuing from the start of energizing the heater 30 (t1) and until the interelectrode voltage $V_S$ of the battery element 12 reaches the predetermined voltage $V_{S1}$ (t2') is the time period TA longer than the judgment time period τS, the heater voltage $V_H$ is kept to 12V. In an air-fuel ratio sensor B in which the heater energizing time period continuing from the start of energizing the heater 30 (t1) and until the interelectrode voltage $V_S$ of the battery element 12 reaches the predetermined voltage $V_{S1}$ (t2) is the time period TB shorter than the judgment time period τS, the heater voltage $V_H$ is changed to 11V at timing t3 when a predetermined time period T1 has further elapsed.

In the air-fuel ratio sensor B in which the temperature is easily raised by energizing the heater 30, therefore, the time period necessary for the interelectrode voltage $V_S$ to reach the activation judging voltage (in the graph, the activation judging voltage $V_L$ in the lean air-fuel ratio region) so that the activation is judged is longer than that in the case where the heater voltage $V_H$ is not switched. As a result, the activation judging timing (t4) of the sensor B can be made closer to the activation judging timing (t4') of the air-fuel ratio sensor A in which the temperature is hardly raised by energizing the heater 30.

According to the embodiment, therefore, the time period necessary for judging the activation of the sensor elements 12 and 14 can be controlled so as to be substantially constant irrespective of the temperature rise characteristics of the air-fuel ratio sensor 10, and the starting characteristics which are exerted after the internal combustion engine is started to operate and before the start of the air-fuel control is enabled can be stabilized to a substantially constant level. In the air-fuel ratio sensor B which is easily activated, the heater voltage $V_H$ is switched from 12V to 11V. Consequently, the phenomenon in which the temperatures of the sensor elements 12 and 14 are excessively raised after the activation judgment can be prevented from occurring.

In the embodiment, the activation judgment for the sensor elements 12 and 14 uses the activation judging voltages $V_{R1}$ and $V_{R2}$ in the rich air-fuel ratio region, and the activation judging voltage $V_L$ in the lean air-fuel ratio region. When the interelectrode voltage $V_S$ is within the voltage range between the activation judging voltages $V_{R1}$ and $V_{R2}$ during the predetermined time period T2 or longer, the sensor elements 12 and 14 are judged to be activated in the exhaust gas in which little oxygen exists and which is obtained when the internal combustion engine is operated in the rich air-fuel ratio region. In contrast, when the interelectrode voltage $V_S$ passes through the voltage range between the activation judging voltages $V_{R1}$ and $V_{R2}$ for a short time period, the operation waits until the interelectrode voltage $V_S$ is lowered to a level which is not higher than the activation judging voltage $V_L$, and, at the timing when $V_S \leq V_L$ is established, the sensor elements 12 and 14 are judged to be activated in the exhaust gas in which oxygen exists abundantly and which is obtained when the internal combustion engine is operated in the lean air-fuel ratio region.

Even when the internal combustion engine is of the type in which the engine is operated at a rich air-fuel ratio for warming up after the start or the like, or the other type in which the engine is operated at a lean air-fuel ratio immediately after the start in order to improve the fuel consumption the exhaust emission, therefore, the air-fuel ratio sensor 10 of the embodiment can judge always correctly the activation of the sensor elements 12 and 14.

In the embodiment, when the sensor elements 12 and 14 are once judged to be activated, the heater voltage $V_H$ is not kept to be as it is, but, after an elapse of the predetermined time period T3 or T4, the heater voltage $V_H$ is lowered by 1V from the initial voltage used in the activation judgment. Thereafter, for each elapse of the predetermined time period T5, the result of control of the pump current $i_P$ conducted by the detection circuit 52 (i.e., the error $\Delta V_S$) is checked to judge whether the pump current $i_P$ is properly controlled or not, or whether or not the sensor elements 12 and 14 are controlled to be within the temperature range in which the air-fuel ratio can be properly detected. If the error $\Delta V_S$ exceeds the allowable range $\pm V_X$, it is judged that the sensor elements 12 and 14 are changed in temperature, and then the heater voltage $V_H$ is changed between the initial voltage and a voltage which is lower than the initial voltage by 1V.

As a result, according to the present invention, the temperatures of the sensor elements 12 and 14 are controlled to be within the temperature range in which the air-fuel ratio can be properly detected. Consequently, the air-fuel ratio can be detected always correctly without being affected by factors such as variation in exhaust gas temperature which is caused by a change in operating conditions of the internal combustion engine.

In the embodiment, when the initial voltage is 11V, the time period continuing from when the sensor elements 12 and 14 are judged to be activated and until when the heater voltage $V_H$ is lowered by 1V from the initial voltage used in the activation judgment is set to be the predetermined time period T4, and, when the initial voltage is 12V, the time period is set to be the predetermined time period T3 which is shorter than the time period T4. This is because the temperatures of the sensor elements 12 and 14 are raised more easily as the heater voltage $V_H$ is higher. The phenomenon in which the temperature of the sensor element is excessively raised after the activation judgment is prevented from occurring, by setting the time periods so that T3<T4.

An embodiment of the present invention is described above. The present invention is not restricted to the embodiment and may be executed in various manners.

Figure 6:
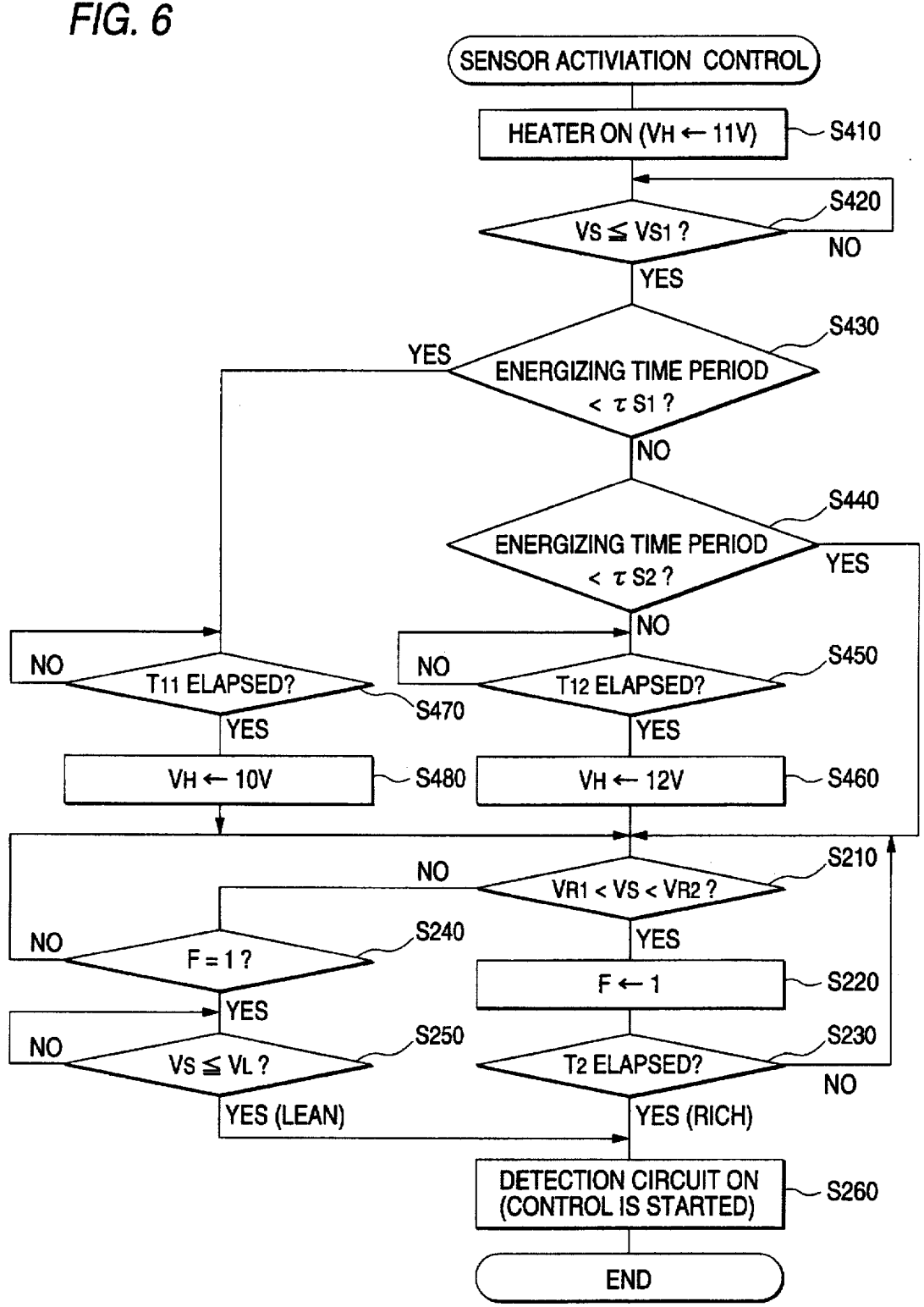
FIG. 6 is a flowchart showing another embodiment of the sensor temperature stabilizing control process.

In the embodiment described above, the sensor activation control process is conducted so that the heater voltage $V_H$ is set to be 12V at the timing when energizing the heater 30 is started at the same time when the internal combustion engine is started to operate, and then lowered to 11V or 10V in sequence. Alternatively, for example, the sensor temperature stabilizing control process may be conducted in the following manner. As shown in FIG. 6, the heater voltage $V_H$ at the start of the heater energizing is set to be 11V (S410). If it is then judged that the interelectrode voltage $V_S$ reaches the predetermined voltage $V_{S1}$ (YES in S420), the heater voltage $V_H$ is changed in such a manner that, if the time period of heater energizing continuing before the judgment is shorter than a judgment time period $\tau S1$ ($\tau S1 < \tau S$) (YES in S430), the heater voltage $V_H$ is changed to 10V after an elapse of a predetermined time period T11 (S470 and S480); if the time period of heater energizing continuing until the interelectrode voltage $V_S$ reaches the predetermined voltage $V_{S1}$ is not shorter than a judgment time period $\tau S2$ ($\tau S2 > \tau S$ and $\tau S1$) (NO in S440), the heater voltage $V_H$ is changed to 12V after an elapse of a predetermined time period T12 (S450 and S460); and, if the time period of heater energizing is within the range between the judgment time periods $\tau S1$ and $\tau S2$, the activation judging operation in S210 and the followings is executed while keeping the heater voltage $V_H$ to 11V.

In this case, a stable point where the control of the pump current $i_P$ is stabilized may be searched in the sensor temperature stabilizing control in the following manner. If the heater voltage at the activation judgment (i.e., the initial voltage) is 10V, the heater voltage $V_H$ is changed from 10V to 11V and vice versa each time when the control error $\Delta V_S$ of the interelectrode voltage $V_S$ exceeds the allowable range $\pm V_X$. If the initial voltage is 12V, the heater voltage $V_H$ is changed from 12V to 11V and vice versa each time when the control error $\Delta V_S$ of the interelectrode voltage $V_S$ exceeds the allowable range $\pm V_X$. If the initial voltage is 11V, the heater voltage $V_H$ is changed to 10V, 11V, and 12V in sequence each time when the control error $\Delta V_S$ of the interelectrode voltage $V_S$ exceeds the allowable range $\pm V_X$.

In the embodiment, in the sensor activation control process, the heater energizing time period continuing from the start of energizing the heater 30 until the interelectrode voltage $V_S$ reaches the predetermined voltage $V_{S1}$ is measured. It is then judged whether the heater voltage $V_H$ is kept to be as it is or switched to another value, on the basis of the measured heater energizing time period. Alternatively, for example, the heater energizing time period necessary for the interelectrode voltage $V_S$ to pass after the start of energizing the heater 30 through a range between arbitrary voltages which are higher than the activation judging voltage $V_{R2}$ in the richest region among the activation judging voltages may be measured. It is then judged whether the heater voltage $V_H$ is kept to be as it is or switched to another value, on the basis of the measured time period.

Figure 7:
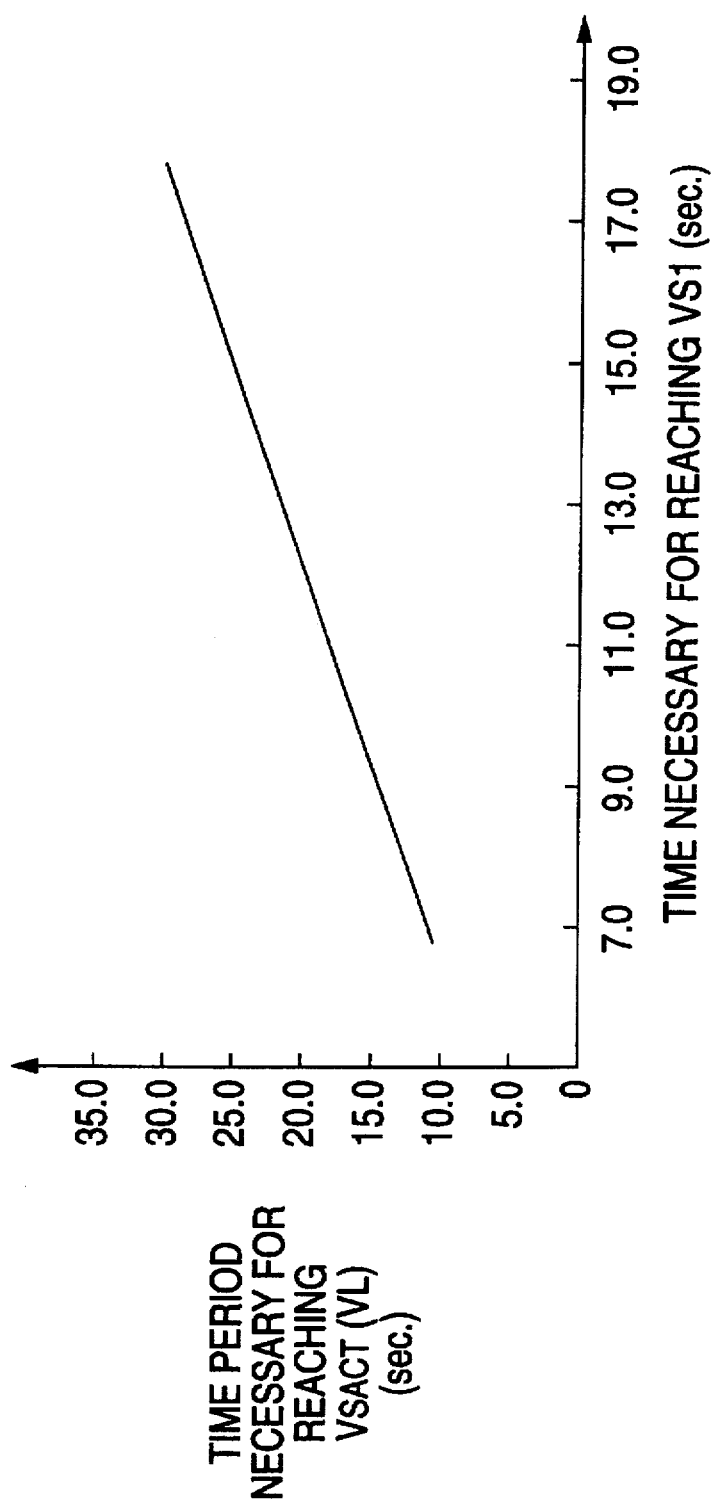
FIG. 7 is a graph showing relationships between the time period necessary for the interelectrode voltage to reach a predetermined voltage $V_{S1}$ and that for the interelectrode voltage to reach an activation judging voltage $V_{SACT}$.

In the embodiment, the time period necessary for the activation of the sensor elements 12 and 14 can be controlled so as to be substantially constant by setting the subsequent heater voltage $V_H$ on the basis of the heater energizing time period, because, as shown in FIG. 7, the heater energizing time period is approximately proportional to the time period necessary for the interelectrode voltage $V_S$ to reach the activation judging voltage $V_{SACT}$. Accordingly, the time period necessary for activation of the sensor elements 12 and 14 is predictable. FIG. 7 shows experimental measurement results of the time period necessary for the interelectrode voltage $V_S$ to reach the predetermined voltage $V_{S1}$ after the start of energizing the heater 30 while setting the heater voltage $V_H$ to be constant (12V), and the time period necessary for the interelectrode voltage $V_S$ to thereafter reach the activation judging voltage $V_{SACT}$ (=$V_L$) in the atmosphere.

In the above, the embodiment of an air-fuel ratio sensor which comprises a pair of sensor elements (the battery element 12 and the pump element 14) and detects the oxygen concentration of the exhaust gas of an internal combustion engine while controlling the pump current $i_p$ flowing through the pump element 14 so that the interelectrode voltage $V_S$ of the battery element 12 is constant has been described. The invention may be applied also to an oxygen sensor of another kind in the same manner as the embodiment. Even in an oxygen sensor in which reference oxygen such as the atmosphere is introduced to one electrode and the oxygen concentration on the side of the other electrode is detected on the basis of the voltage across the electrodes, or an oxygen sensor of the limiting current type which detects the oxygen concentration while causing a limiting current to flow through electrodes, for example, the time period necessary for activating a sensor element can be stabilized. In other words, the invention may be applied to an oxygen sensor of any kind and attain the same effects as described above as far as the oxygen sensor comprises a sensor element in which porous electrodes are disposed on both faces of a solid electrolyte made of zirconia or the like and a heater for heating the sensor element.

What is claimed is:

1. A method of controlling the energizing of a heater for an oxygen sensor, said oxygen sensor including a first sensor element having a pair of porous electrodes disposed on both faces of a solid electrolyte, said solid electrolyte being oxygen-ion-conductive, and a heater being disposed in the vicinity of said first sensor element and being energized to heat said first sensor element, said method comprising the steps of:

starting to energize said heater to heat said first sensor element;

measuring at least one of a time period from the start of energizing until an interelectrode voltage, generated between said pair of porous electrodes, reaches a predetermined voltage which is higher than an activation judging voltage, and a time period during which said interelectrode voltage maintains a voltage value which lies in a predetermined range of voltage values, each of which is greater than said activation judging voltage;

judging whether said first sensor element is activated based on a length of said at least one time period; and setting an energizing condition of said heater based on said length of said time period.

2. A method according to claim 1, further comprising the step of:

when said interelectrode voltage reaches said predetermined voltage within a judgment time period, lowering after a predetermined period of time, a voltage used to energize said heater.

3. A method according to claim 1, further comprising the step of:

when said interelectrode voltage reaches said predetermined voltage after a judgment time period, increasing, after a predetermined period of time, a voltage used to energize said heater.

4. A method according to claim 1, wherein said step of setting said energizing condition comprises the step of setting a voltage which is required to energize said heater based on said at lest one time period.

5. A method according to claim 4, wherein said step of setting a voltage decrease said voltage as said at least one time period decreases.

6. A method according to claim 1, said oxygen sensor further including a second sensor element having a pair of porous electrodes disposed on both fact of a solid electrolyte, said solid electrolyte being oxygen-ion-conductive, and a measurement gas chamber formed between said first and second sensor elements, said second sensor element being disposed so that one porous electrode is in contact with said measurement gas chamber and the other porous electrode is in contact with a surrounding measured gas atmosphere, said method further comprising the steps of:

after judging activation of said first sensor element, controlling a current for energizing said second sensor element so that said interelectrode voltage of said first sensor element reaches a predetermined target voltage; and changing said energizing condition of said heater in accordance with an error of said interelectrode voltage of said first sensor element with respect to said predetermined target voltage so that said error is within a predetermined allowable range to stabilize a temperature of said first sensor element.

7. An apparatus for controlling the energizing of a heater for an oxygen sensor, said apparatus being disposed in an oxygen sensor comprising a first sensor element having a pair of porous electrodes disposed on both faces of a solid electrolyte, said solid electrolyte being oxygen-ion-conductive; a heater being disposed in the vicinity of said first sensor element and being energized to heat said first sensor element; voltage detecting means for detecting an interelectrode voltage generated between said pair of porous electrodes by causing a current to flow through said first sensor element; and judging means for judging whether said first sensor element is activated when said interelectrode voltage detected by said voltage detecting means reaches a predetermined activation judging voltage; said apparatus comprising:

energizing means for energizing said heater to cause said heater to generate heat;

time measuring means for measuring at least one of a time period from the start of energizing until said interelectrode voltage generated between said pair of porous electrodes reaches a predetermined voltage which is higher than said predetermined activation judging voltage, and a time period during which said interelectrode voltage maintains a voltage value which lies in a predetermined range of voltage values, each of which is greater than said predetermined activation judging voltage; and setting means for setting an energizing condition based on a length of said at least one time period.

8. An apparatus according to claim 7, wherein, when said interelectrode voltage reaches said predetermined voltage within a judgement time period, said energizing means being arranged to decrease, after a predetermined period of time, a voltage required to energize said heater.

9. An apparatus according to claim 7, wherein, when said interelectrode voltage reaches said predetermined voltage after a judgement time period, said energizing means being arranged to increase, after a predetermined period of time, a voltage used to energize said heater.

10. An apparatus according to claim 7, wherein said energizing means is arranged to set said energizing condition so that a voltage used to energize said heater is decreased as said at least one time period decreases.

11. An apparatus according to claim 7, wherein said setting means sets a voltage to energize said heater based on said at least one time period.

12. An apparatus according to claim 11, wherein said setting means decreases said voltage as said at least one time period decreases.

13. An apparatus according to claim 7, said oxygen sensor further comprising a second sensor element having a pair of porous electrodes disposed on both faces of a solid electrolyte, said solid electrolyte being oxygen-ion-conductive; a measurement gas chamber formed between said first and second sensor elements, said second sensor element being disposed so that one porous electrode is in contact with said measurement gas chamber and the other porous electrode is in contact with a surrounding measured gas atmosphere; detecting means for controlling a current for energizing said second sensor element so that said interelectrode voltage of said first sensor element reaches a predetermined target voltage, said detection means outputting the energizing current as a detection signal indicative of an oxygen concentration of the surrounding measured gas chamber atmosphere; said apparatus further comprising stabilizing means for changing the conditions for energizing said heater, after said activation judging means judges that said first sensor element is activated, in accordance with an error of said interelectrode voltage of said first sensor element, controlled by said detection circuit, with respect to said predetermined target voltage, so that the error is within a preset allowable range to stabilize a temperature.

* * * * *